United States Patent
Sathe et al.

(10) Patent No.: US 9,951,012 B2
(45) Date of Patent: Apr. 24, 2018

(54) PROCESS FOR THE PREPARATION OF (3R,4R)-(1-BENZYL-4-METHYLPIPERIDIN-3-YL)-METHYLAMINE

(71) Applicant: UNICHEM LABORATORIES LIMITED, Mumbai (IN)

(72) Inventors: Dhananjay G. Sathe, Thane (IN); Arijit Das, Kolkata (IN); Yogesh Subhash Patil, Aurangabad (IN); Nilesh L. Bonde, Baroda (IN); Ankush Sampat Kekan, Pune (IN)

(73) Assignee: UNICHEM LABORATORIES LIMITED, Mumbai (IN)

( * ) Notice: Subject to any disclaimer, the term of this patent is extended or adjusted under 35 U.S.C. 154(b) by 0 days.

(21) Appl. No.: 14/891,028

(22) PCT Filed: Dec. 2, 2014

(86) PCT No.: PCT/IB2014/066510
§ 371 (c)(1),
(2) Date: Nov. 13, 2015

(87) PCT Pub. No.: WO2015/087201
PCT Pub. Date: Jun. 18, 2015

(65) Prior Publication Data
US 2016/0102057 A1    Apr. 14, 2016

(30) Foreign Application Priority Data
Dec. 9, 2013    (IN) .......................... 3843/MUM/2013

(51) Int. Cl.
*C07D 211/02* (2006.01)
*C07D 211/56* (2006.01)
(Continued)

(52) U.S. Cl.
CPC .......... *C07D 211/02* (2013.01); *C07D 211/56* (2013.01); *C07D 211/72* (2013.01); *C07D 213/74* (2013.01); *C07D 213/75* (2013.01)

(58) Field of Classification Search
CPC .................................................. C07D 211/02
See application file for complete search history.

(56) References Cited

U.S. PATENT DOCUMENTS 7,301,023 B2 * 11/2007 Flanagan .............. C07D 487/04
544/280
8,232,394 B2 *  7/2012 Ruggeri ................ C07D 211/56
544/280
(Continued)

OTHER PUBLICATIONS

Brown Ripin "Development of a Scaleable Route for the Production of cis-N-Benzyl-3-methylamino-4-methylpiperidine" Organic Process Research & Development 2003, 7, 115-120.*
Cai "Investigation of Practical Routes for the Kilogram-Scale Production of cis-3-Methylamino-4-methylpiperidines" Organic Process Research & Development 2005, 9, 51-56.*
Baxter "Reductive Aminations of Carbonyl Compounds with Borohydride and Borane Reducing Agents." Chapter 1, Organic Reactions 2002, 59, 1-714.*
Rosenkranz Journal of Organic Chemistry 1956, 21, 520-522.*
Jones J. Chem. Soc. Perkin Trans. 11987, 2585-2592.*
McMurry, John "Organic Chemistry with Biological Applications" 3rd Edition, Cengage: Stamford, 2011, p. 384.*
(Continued)

*Primary Examiner* — David K O'Dell
(74) *Attorney, Agent, or Firm* — Banner & Witcoff, Ltd.

(57) ABSTRACT

The present invention is related to an improved and efficient process for preparation of (3R,4R)-(1-benzyl-4-methylpiperidin-3-yl)-methylamine which comprises:
(a) N-acylation of 3-Amino-4-methyl pyridine; (b) Quarternization of 3-Acetylamino-4-methyl pyridine using benzyl halide; (c) Partial reduction of quarternized 3-Acetylamino-4-methyl pyridine by Sodium borohydride in Methanol or water; (d) Hydrolysis of partially reduced product to 1-Benzyl-4-methylpiperidin-3-one in presence of acid; (e) Reductive amination of 1-Benzyl-4-methylpiperidin-3-one using Methanolic methylamine in presence of Titanium(IV) isopropoxide in Methanol; (f) Resolution of 1-Benzyl-4-methylpiperidin-3-yl)-methylamine using Ditoluoyl (L) tartaric acid to get (3R,4R)-(1-benzyl-4-methylpiperidin-3-yl)-methylamine. The invention is also related to novel intermediates:

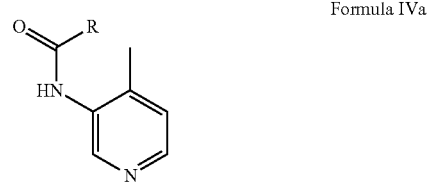

Formula IVa

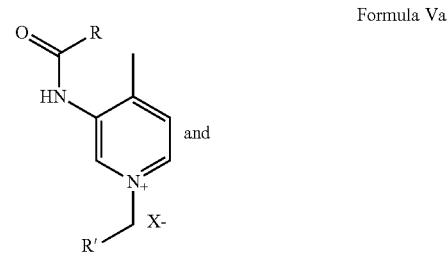

Formula Va
and

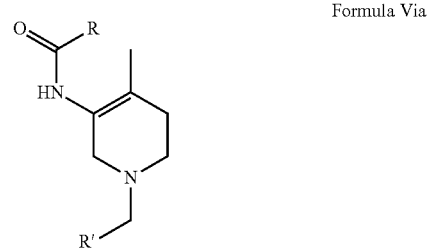

Formula VIa wherein R, R' and X are as described in the specification.

17 Claims, No Drawings

(51) Int. Cl.
*C07D 213/75* (2006.01)
*C07D 213/74* (2006.01)
*C07D 211/72* (2006.01)

(56) References Cited

U.S. PATENT DOCUMENTS

2004/0229923 A1 11/2004 Wilcox et al.
2010/0035903 A1 2/2010 Blumenkopf et al.
2010/0291026 A1 11/2010 Rao et al.

OTHER PUBLICATIONS

Clayden "Organic Chemistry" 2nd Ed. Oxford: 2012, p. 30.*
Steadman's Medical Dictionary entry for "X" Online "http://www.stedmansonline.com/content/mlr20100624151645091238509" accessed Feb. 22, 2007.*
Greene and Wuts, Protective Groups in Organic Synthesis 3rd edition Wiley: New York, 1999 pp. 494-615.*
International Search Report and Written Opinion dated Apr. 22, 2015 (PCT/IB2014/066510); ISA/US.
PubChem Compound Summary for CID 59203741 Create Date: Aug. 20, 2012 (Aug. 20, 2012) p. 3, Fig.
Iorio et al. "Synthesis and Conformation Study of Some Diastereoisomeric 4-Methyi-3-Phenyl-3-Piperidinols and Related Esters", Tendedron., 1970, vol. 26, pp. 5519-5527. p. 5520, scheme 1.

* cited by examiner

PROCESS FOR THE PREPARATION OF (3R,4R)-(1-BENZYL-4-METHYLPIPERIDIN-3-YL)-METHYLAMINE

CROSS-REFERENCE TO RELATED APPLICATIONS

The present application is a U.S. National Phase filing of International Application No. PCT/IB2014/066510, filed on Dec. 2, 2014, designating the United States of America and claiming priority to Indian Patent Application No. 3843/MUM/2013, filed Dec. 9, 2013, and this application claims priority to and the benefit of the above-identified applications, which are all incorporated by reference herein in their entireties.

TECHNICAL FIELD

The present invention provides an efficient and improved process for the preparation of (3R,4R)-(1-benzyl-4-methyl-piperidin-3-yl)-methylamine; a key starting material for the synthesis of 3-{(3R,4R)-4-methyl-3-[methyl(7H-pyrrolo[2,3-d]pyrimidin-4-yl)amino]piperidin-1-yl}-3-oxo-propanenitrile.

BACKGROUND OF THE INVENTION

3-{(3R,4R)-4-methyl-3-[methyl(7H-pyrrolo[2,3-d]pyrimidin-4-yl)amino]piperidin-1-yl}-3-oxo-propanenitrile, 2-hydroxypropane-1,2,3-tricarboxylate described as FORMULA I below and as disclosed in WO 02/096909, U.S. Pat. No. 7,301,023. US FDA approved it for rheumatoid arthritis.

FORMULA I

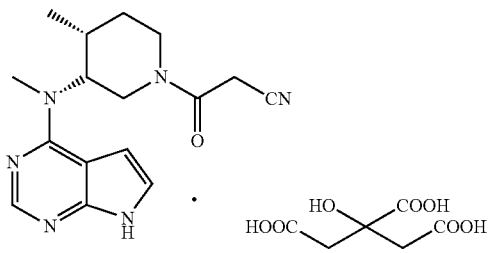

The key step for the preparation of 3-{(3R,4R)-4-methyl-3-[methyl(7H-pyrrolo[2,3-d]pyrimidin-4-yl)amino]piperidin-1-yl}-3-oxo-propanenitrile as depicted in (Scheme-1) WO 02/096909 includes:
  (i) resolution of racemic (1-Benzyl-4-methylpiperidin-3-yl)-methylamine to (3R,4R)-(1-Benzyl-4-methylpiperidin-3-yl)-methylamine using Di-p-toluoyl-L-tartarate;
  (ii) condensation of 4-Chlropyrrolo[2,3-d]pyrimidine with (3R,4R)-(1-Benzyl-4-methylpiperidin-3-yl)-methylamine to get (3R,4R)-(1-benzyl-4-methylpiperidin-3-yl)methyl-(7H-pyrrolo[2,3-d]pyrimidin-4-yl)-amine; and
  (iii) debenzylation of (3R,4R)-(1-Benzyl-4-methylpiperidin-3-yl)methyl-(7H-pyrrolo[2,3-d]pyrimidin-4-yl)-amine followed by condensation with cyano acetic acid derivative to get 3-{(3R,4R)-4-methyl-3-[methyl(7H-pyrrolo[2,3-d]pyrimidin-4-yl)amino]piperidin-1-yl}-3-oxo-propanenitrile (FORMULA I), (Scheme-1).

Scheme-1

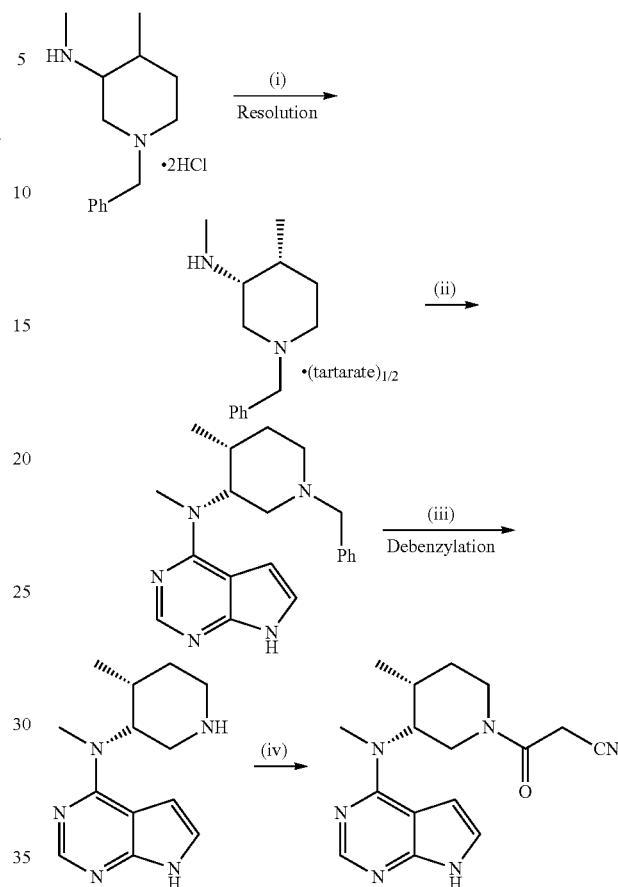

The most important part for the preparation of FORMULA I is the synthesis of (3R,4R)-(1-Benzyl-4-methylpiperidin-3-yl)-methylamine as it is very tedious synthesis and also requires very expensive reagent. There are several processes reported in literature for the synthesis and resolution of racemic (1-Benzyl-4-methylpiperidin-3yl)-methylamine to (3R,4R)-(1-Benzyl-4-methylpiperidin-3-yl)-methylamine.

WO 2007/012953 discloses preparation of 1-Benzyl-3-methoxycarbonylamino-4-methyl-pyridinium bromide and it's asymmetric reduction using mixture of Ruthenium and Iridium based chiral catalysts under hydrogenation condition to provide (3R,4R)-(1-Benzyl-4-methylpiperidin-3-yl)-methylamine with 84% cis isomer, having 68% ee.

The patent further discloses the preparation of same intermediate by applying partial reduction followed by asymmetric reduction approach to obtain highly enriched Piperidine derivative as depicted in Scheme-2.

Scheme-2

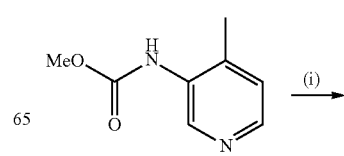

-continued

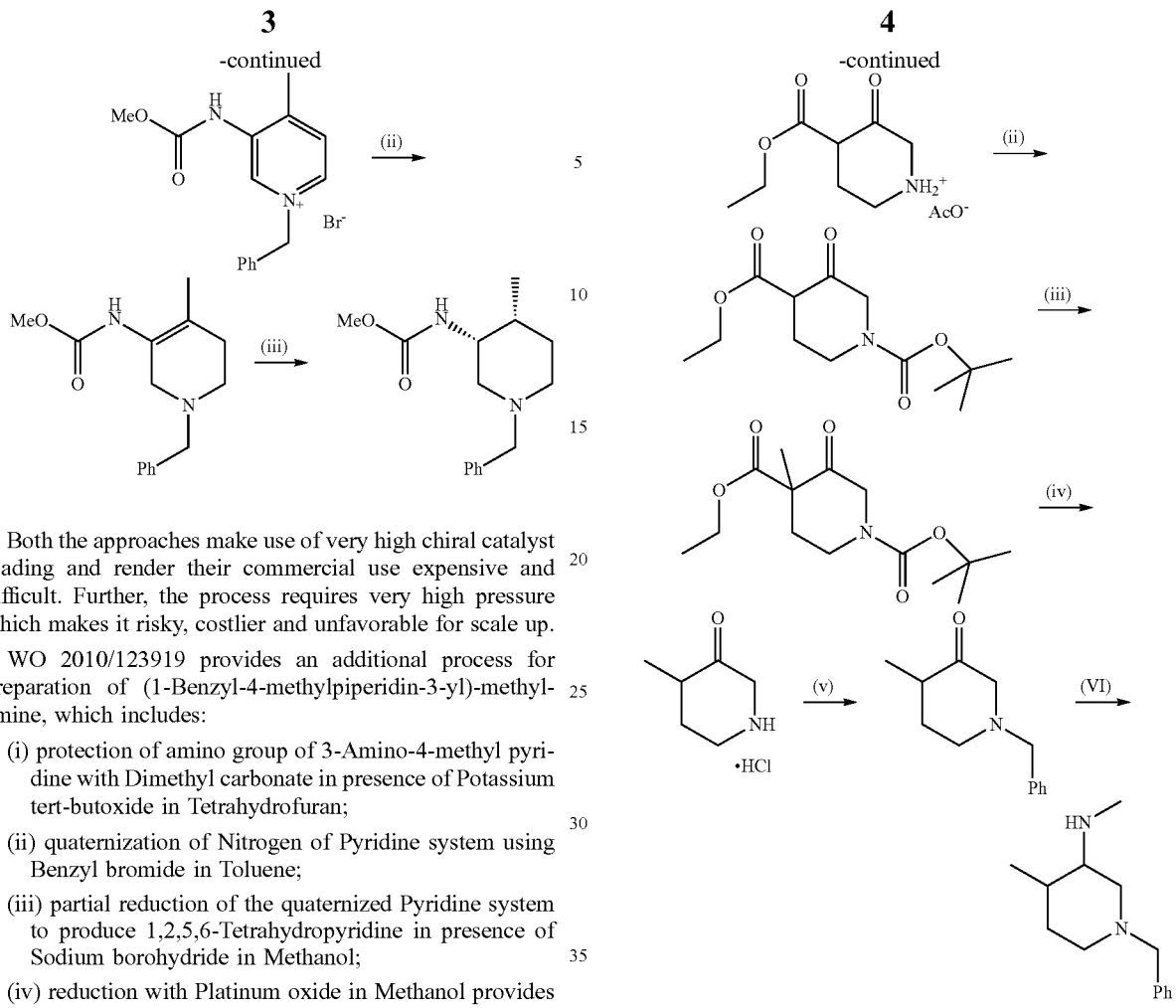

Both the approaches make use of very high chiral catalyst loading and render their commercial use expensive and difficult. Further, the process requires very high pressure which makes it risky, costlier and unfavorable for scale up.

WO 2010/123919 provides an additional process for preparation of (1-Benzyl-4-methylpiperidin-3-yl)-methylamine, which includes:

(i) protection of amino group of 3-Amino-4-methyl pyridine with Dimethyl carbonate in presence of Potassium tert-butoxide in Tetrahydrofuran;

(ii) quaternization of Nitrogen of Pyridine system using Benzyl bromide in Toluene;

(iii) partial reduction of the quaternized Pyridine system to produce 1,2,5,6-Tetrahydropyridine in presence of Sodium borohydride in Methanol;

(iv) reduction with Platinum oxide in Methanol provides Piperidine derivative. Followed by the purification by column chromatography; and (v) further reaction with Lithium aluminium hydride and purification by column chromatography to get (1-Benzyl-4-methyl-piperidin-3-yl)-methylamine.

The process has several drawbacks. Overall process yield is very poor i.e. approximately 40%. The process uses column chromatography at two stages. Lithium aluminum hydride, a known pyrophoric reagent, account for the safety risk during its manufacturing. Lastly Platinum oxide is very explosive in presence of hydrogen. It is very costly reagent which discourages its use on plant scale. Overall the process is costlier, not so safe to work on commercial scale and demands stringent skill of art.

WO 2010/123919 further reveals an additional procedure for the preparation of (1-Benzyl-4-methylpiperidin-3-yl)-methylamine and the synthetic procedure is summarized in Scheme-3.

Scheme-3

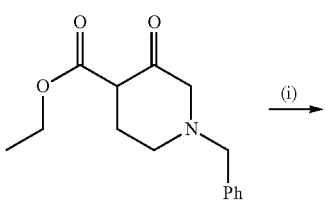

Process involves debenzylation and quaternization of ethyl 1-Benzyl-3-oxopiperidine-4-carboxylate followed by protection of the resulted Ethyl 3-oxopiperidine-4-carboxylate derivative using di-tert-butyl dicarbonate. Protected Piperidine derivative was methylated by abstracting the Methylenic proton using Sodium hydride and further reaction with Iodomethane. In the next stage deprotection of N-tert-butoxycarbonyl group was carried out in acidic media, and the resulting 4-Methylpiperidin-3-one was benzylated followed by reductive amination with Methylamine and Sodium triacetoxyborohydride provide the desired product (1-Benzyl-4-methylpiperidin-3-yl)-methylamine.

The overall conversion involves five stages from quite a complex starting material. The process involves protection and deprotection in different stages. Use of costly, non safe reagents such as Sodium hydride and lacrimatic Benzyl bromide and Sodium triacetoxyborohydride limit its commercial scale production. The process has major draw back with respect to the use of column chromatography at three stages. Moreover disclosure of process is silent about the purity of intermediates and of the target molecule produced. The overall yield mentioned for the process is also very low i.e. 13.6 molar percent.

U.S. Pat. No. 6,627,754 provides a similar reductive amination route as discussed in WO 2010/123919 for the synthesis of (1-Benzyl-4-methyl piperidin-3-yl)-methylamine from 1-Benzyl-4-methylpiperidin-3-one in a sealed tube using Sodium triacetoxyborohydride as a reducing agent.

Sodium triacetoxyborohydride is extremely moisture sensitive pyrophoric reagent. Sealed tube reaction is difficult to execute on large scale.

The processes taught by prior art have several drawbacks namely expensive, not suitable for scale up at plant level, energy intensive, difficult, giving lower yields, forcing use of corrosive acids, longer duration of corrosive reactions and less user friendly. Considering the drawbacks of prior art and very complex methodologies applied, for the preparation of the (1-Benzyl-4-methyl piperidin-3-yl)-methylamine, there is a urgent and pressing need for simple, energy economical, financially cheaper plant friendly process, environment friendly process for the preparation of (3R,4R)-(1-Benzyl-4-methylpiperidin-3-yl)-methylamine to synthesize FORMULA I that does not use hygroscopic and pyrophoric chemicals and yet provides better yields.

SUMMARY OF THE INVENTION

An object of the present invention is to provide an improved and efficient process for the preparation of (1-Benzyl-4-methylpiperidin-3-yl)-methylamine which has better over all yield.

Another object of the invention is to provide a cost effective, environment friendly and energy economic process to prepare (3R,4R)-(1-Benzyl-4-methylpiperidin-3-yl)-methylamine Yet another object of the invention is to provide a process for the synthesis of (3R,4R)-(1-Benzyl-4-methylpiperidin-3-yl)-methylamine to prepare 3-{(3R,4R)-4-methyl-3-[methyl (7H-pyrrolo[2,3-d]pyrimidin-4-yl)amino]piperidin-1-yl}-3-oxo-propanenitrile, 2-hydroxypropane-1,2,3-tricarboxylate (FORMULA I).

According to a first aspect of the present invention an improved and efficient process for the preparation of (3R,4R)-(1-Benzyl-4-methylpiperidin-3-yl)-methylamine, of the Formula II is provided.

Another aspect of the present invention is to provide a process for the preparation of a compound of Formula IIa, as depicted in Scheme-4, comprising:
  (i) N-acylation of 3-Amino-4-methyl pyridine (Formula III) with alkyl, aryl or substituted aryl acid anhydride or acid chloride to get Formula IVa;
  (ii) quaternization of Nitrogen of Pyridine system having Formula IVa, using Benzyl or substituted Benzyl halide in an organic solvent or aqueous solvent or mixture(s) thereof to get Formula Va;
  (iii) partial reduction of the optionally isolated quaternized pyridine system having Formula Va to produce 1,2,5,6-Tetrahydropyridine system of Formula VIa in the presence of a reducing agent or any Borohydride agent in an organic solvent or aqueous solvent or mixture(s) thereof, at an ambient temperature;
  (iv) hydrolysis of 1,2,5,6-Tetrahydropyridine system of Formula VIa in presence of an acid or mixture of acids to get Formula VIIa, at an ambient temperature;
  (v) reductive amination of Formula VIIa using Methylamine in presence of any Lewis acids in an organic solvent or aqueous solvent or mixture(s) thereof followed by reduction using any reducing agent or any alkali metal Borohydride derivatives produce compound of Formula VIIIa, at an ambient temperature; and
  (vi) further resolution of compound VIIIa in presence of any resoluting agent in an organic solvent or aqueous solvent or mixture(s) thereof produce compound of Formula IIa.

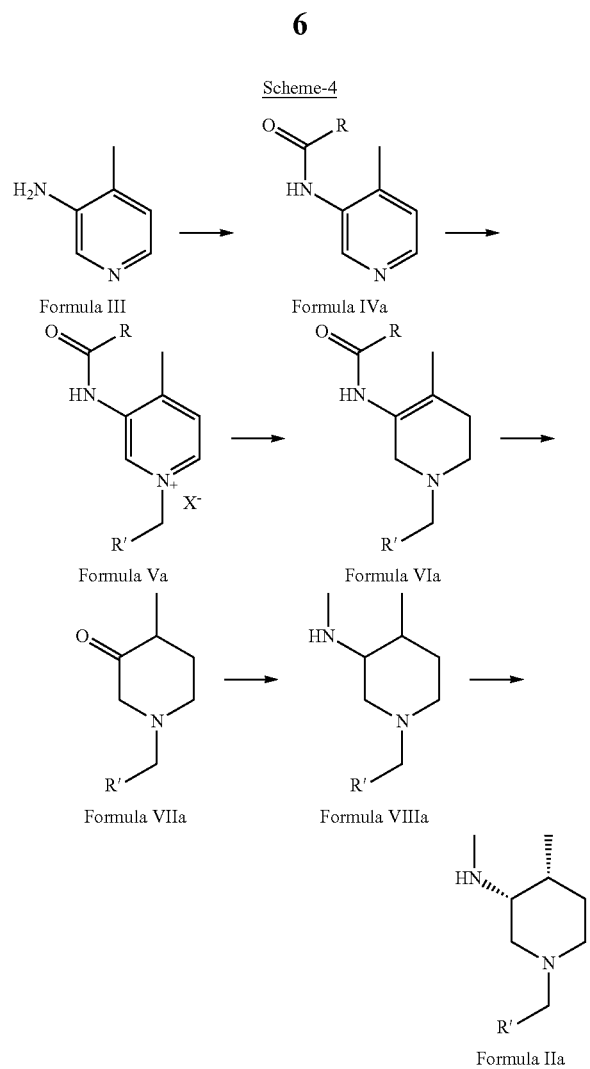

Scheme-4 wherein R represents hydrogen, alkyl, aryl, substituted aryl and R' represents aryl or substituted aryl group.

Prior art WO 2010/123919 uses reactants of different class of compounds. The two routes of synthesis (ROS) are dissimilar. WO 2010/123919 does not envisage use of anhydride in the first step. The intermediate formed in the reaction of the present invention has a Methyl in the side chain which is not the case with prior art. Initial use of different class of reactants produces different classes of intermediates. Hydrolysis and reductive amination steps and the intermediates formed are unique to the ROS of the present invention. These are absent in the prior art. Lithium Aluminium Hydride is essential in WO 2010/123919 but is absent in present invention. Inventive step of the present invention also resides in surprisingly reduced durations of various reaction steps as compared to those in WO 2010/123919. Preparation of 1,2,5,6-Tetrahydropyridine system of Formula VIa can be completed 30% of time required by WO 2010/123919.

Yet another aspect of the present invention is to provide a process for the preparation of (3R,4R)-(1-benzyl-4-methylpiperidin-3-yl)-methylamine of Formula (II), as depicted in Scheme 5, comprising:
  (i) N-acylation of 3-amino-4-methyl pyridine with Acetyl chloride or Acetic anhydride to get Formula IV;
  (ii) quaternization of Nitrogen of pyridine system having Formula IV, using Benzyl chloride in presence of toluene to get Formula V;

(iii) partial reduction of the optionally isolated quaternized Pyridine system of Formula V to produce 1,2,5,6-Tetrahydropyridine system of Formula VI in presence of Sodium borohydride in Methanol or water to get Formula VI, at an ambient temperature;

(iv) hydrolysis of 1,2,5,6-Tetrahydropyridine system of Formula V in presence of mixture of Hydrochloric acid and Acetic acid to get Formula VII, at an ambient temperature;

(v) reductive amination of Formula VII in presence of Titanium(IV) tetraisopropoxide in Methylamine followed by reduction with Sodium borohydride to get 1-Benzyl-4-methylpiperidin-3-yl)-methylamine of Formula VIII, at an ambient temperature; and (vi) further resolution of compound of Formula VIII in presence of a resoluting agent such as Dibenzoyl-L-tartaric acid or Ditoluoyl-L-tartaric acid in the mixture of methanol and/or water to produce (3R,4R)-(1-Benzyl-4-methylpiperidin-3-yl)-methylamine of the Formula II.

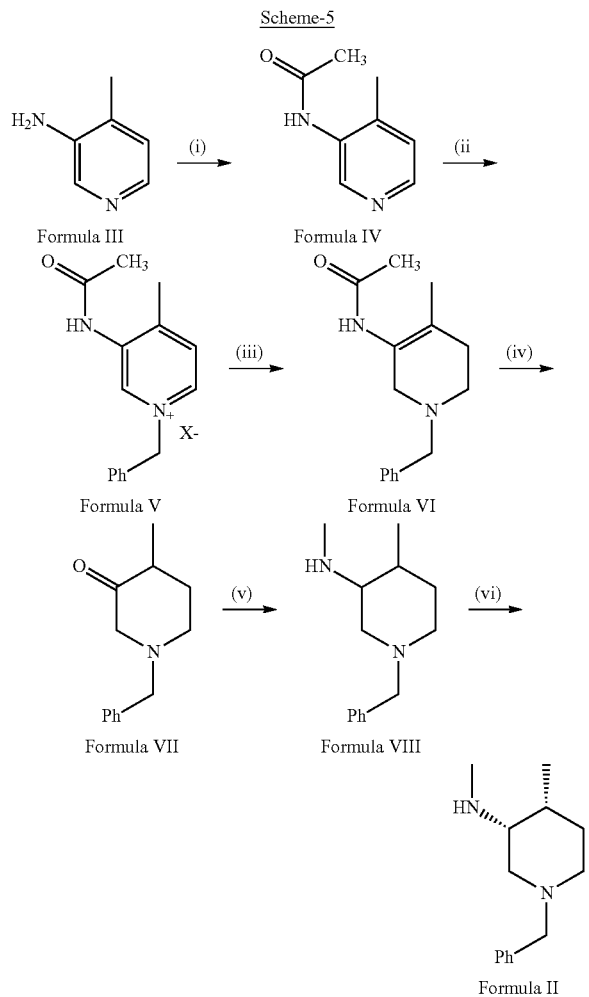

Scheme-5

Reagent: (i) Acetyl chloride, acetic acid, room temperature; (ii) Benzylchloride, toluene, 110° C.; (iii) Sodium borohydride, methanol, 0° C. to 5° C. or sodium borohydride, water, 0° C. to 5° C.; (iv) HCl, AcOH, 80° C. to 85° C.; (v) Titanium(IV) tetraisopropoxide, methanolic methylamine, $NaBH_4$, MeOH, 0° C. to 5° C.; (vi) Ditoluoyl-L-tartaric acid, MeOH-water (1:1)

DETAILED DESCRIPTION OF THE INVENTION

The present invention relates to an improved and efficient process for the preparation of compound of formula (IIa) comprising:

i) N-acylation of 3-amino-4-methyl pyridine (Formula III) with alkyl, aryl or substituted aryl acid anhydride or acid chloride to get Formula IVa;

(ii) quaternization of Nitrogen of Pyridine system having Formula IVa, using Benzyl or substituted Benzyl halide in an organic solvent to get Formula Va;

(iii) partial reduction of the quaternized pyridine system having Formula Va to produce 1,2,5,6-Tetrahydropyridine system of Formula VIa in presence of a reducing agent or any Borohydride agent in an organic solvent, at an ambient temperature;

(iv) hydrolysis of 1,2,5,6-Tetrahydropyridine system of Formula VIa in presence of acid or mixture of acids to get Formula VIIa, at an ambient temperature;

(v) reductive amination of Formula VIIa using Methylamine in presence of any Lewis acids in an organic solvent or aqueous solvent or mixture(s) thereof followed by reduction using any reducing agent or any alkali metal borohydride derivatives produce compound of Formula VIIIa, at an ambient temperature; and (vi) further resolution of compound VIIIa in presence of any resoluting agent in an organic solvent or aqueous solvent or mixture(s) thereof produce compound of Formula IIa C1 acid anhydride is an anhydride of Acetic acid i.e. Acetic anhydride. C2 acid anhydride is an anhydride of Propanoic acid. In the present invention one may use anhydrides of C1-10 acids. C1-10 Acid chloride is to be construed as Acid chloride of Formic acid to Decanoic acid, aryl acid chlorides or substituted acid chlorides having upto 10 carbon atoms. C1-C5 alcohols are to be construed as Methnol, Ethanol, Propanol, Butanol and Pentanol. Better overall yield is to be interpreted as overall yield more than 50% for the synthesis of 1-Benzyl-4-methylpiperidine-3-yl)-methylamine an intermediate before resolution.

Terms quaternization and quaternization are used interchangeably and have the same meaning with respect to attachments to tertiary Nitrogen. Terms improved and efficient are to be construed in view of better yields, less energy intensive, reactions of shorter durations besides reduced costs of inputs and simplicity of the procedures involved, better scalability to plant level. Pyridine system means pyridine ring portion in the molecular structure with or without substituents. Ambient temperature is to be interpreted as temperature between 0° C. to 30° C. RT is room temperature. Terms Methylene chloride and Methylene dichloride i.e. MDC are used interchangeably. The inventive step of the present invention resides in (Scheme-6):

(i) N-acylation of 3-Amino-4-methyl pyridine (Formula III) with alkyl, aryl or substituted aryl acid anhydride or acid chloride to get Formula IVa. Prior art is devoid of acetylation reaction at this stage. Prior art teaches use of Dimethyl carbonate and due to difference in reactants of this initial stage, structurally different intermediates are formed belonging to different classes of chemical compounds exhibiting different properties;

(ii) quarternization of Nitrogen of Pyridine system having Formula IVa, using Benzyl or substituted Benzyl halide in an organic solvent to get Formula Va;

(iii) partial reduction of the optionally isolating quarternized Pyridine system having Formula Va to produce 1,2,5,6-Tetrahydropyridine system of Formula VIa in presence of a reducing agent or any borohydride agent in an organic solvent at an ambient temperature;

(iv) hydrolysis of 1,2,5,6-Tetrahydropyridine system of Formula VIa in presence of acid or mixture of acids to get Formula VIIa at an ambient temperature; and (v) reductive amination of Formula VIIa using Methylamine in presence of any Lewis acids in an organic solvent or aqueous solvent or mixture(s) thereof followed by reduction using any reducing agent or any alkali metal borohydride derivatives produce compound of Formula VIIIa at an ambient temperature.

Scheme-6

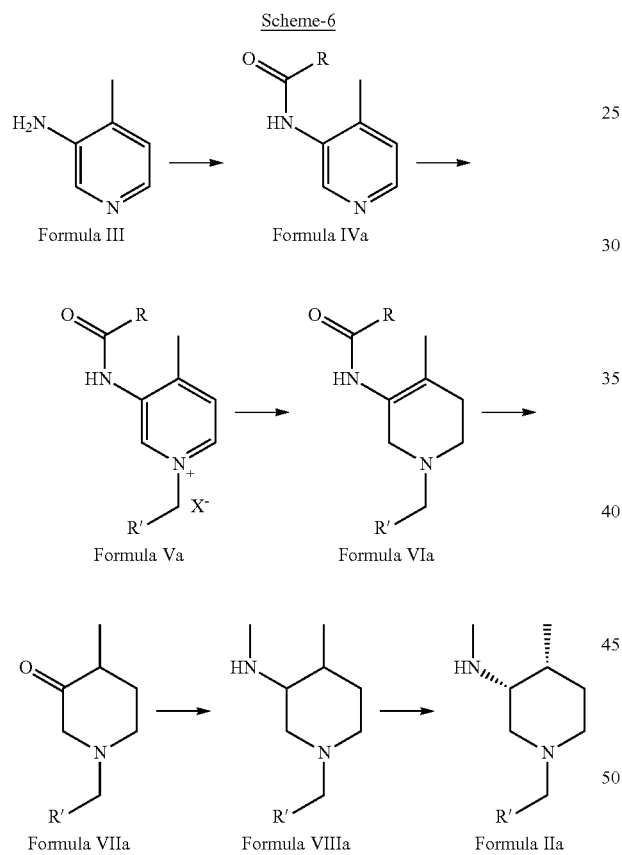

wherein R represents hydrogen, alkyl, aryl, substituted aryl and R' represents aryl or substituted aryl group.

N-acylation of 3-Amino-4-methyl pyridine (Formula III) with alkyl, aryl or substituted aryl acid anhydride includes C1-10 anhydride, acetic anhydride, and more preferably acetic anhydride.

N-acylation of 3-Amino-4-methyl pyridine (Formula III) with alkyl, aryl or substituted aryl acid chloride includes C1-10 acid chloride, acetyl chlorides, benzoyl chloride etc. more preferably acetyl chloride. N acylation leads to formation of the compound of the formula (IVa) and salts thereof,

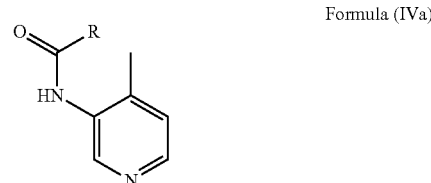

wherein R represents C1-C10 alkyl, aryl or substituted aryl, but not including iso-propyl, t-butyl and phenyl. When R represents C3-C10 alkyl, aryl or substituted aryl, but not including iso-propyl, t-butyl and phenyl, novel compounds are formed.

Quarternization of Nitrogen of Pyridine system having Formula IVa, using benzyl or substituted benzyl halide includes Benzyl chloride, Benzyl bromides etc. more preferably benzyl chloride.

Quarternization of Nitrogen of Pyridine system having Formula IVa, to get Formula Va is carried out using Benzyl halide or substituted benzyl halide in presence of an organic or aqueous-organic solvent which includes Toluene, Xylenes, alcoholic solvents, ethereal solvents more preferably Toluene and Xylenes most preferably Toluene. Polar, protic, aprotic solvents are to be interpreted as per prevailing definitions.

Quarternization of Nitrogen of Pyridine system having Formula IVa, using benzyl or substituted benzyl halide in presence of an organic solvent to get Formula Va was carried out at temperature between 40° C. to 110° C. more preferably between 75° C. to 85° C. A compound of the formula (Va)

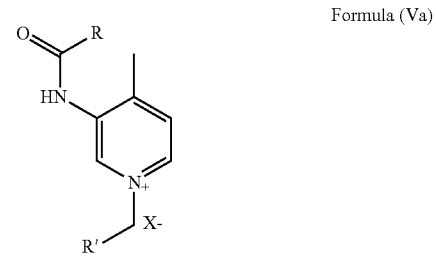

wherein R represents alkyl, aryl or substituted aryl more preferably methyl; R' represents aryl or substituted aryl group more preferably phenyl; and X represents halides group such as chloro, bromo, iodo, or any leaving group such as tosyloxy or mesyloxy.

Partial reduction of the quarternized pyridine system of Formula Va produces 1,2,5,6-Tetrahydropyridine system of Formula VIa, in presence of a reducing agent such as borohydride agent including Sodium borohydride, Sodium cyanoborohydride, Sodium triacetoxyborohydride more preferably Sodium borohydride and the organic solvent selected from the group consisting of alcoholic solvents such as Methanol, Ethanol ethereal solvents such as Di-isopropyl ether (DIPE), Methyl tertiary butyl ether (MTB) or Toluene, Xylenes or aqueous mixture thereof more preferably Methanol, water most preferably water. The reduction using the borohydride reagent was carried out between 0° C. to 10° C. more preferably between 0° C. to 5° C.

1,2,5,6-Tetrahydropyridine system of Formula VIa can be obtained from Pyridine system having Formula IVa optionally isolating quarternized Pyridine system having Formula Va. A compound of the formula (VIa) and salts thereof

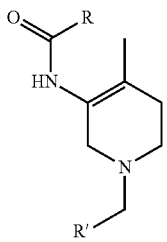

Formula (VIa)

wherein R represents alkyl, aryl or substituted aryl more preferably methyl;

R' represents aryl or substituted aryl group more preferably phenyl.

Hydrolysis of 1,2,5,6-Tetrahydropyridine system of Formula VIa in presence of an acid or mixture of acids which includes Hydrochloric acid, Sulfuric acid, Phosphoric acid, Trifluoroacetic acid, Trichloroacetic acid, acetic acid or aqueous solutions thereof or mixture(s) thereof more preferably Hydrochloric acid and Acetic acid most preferably mixture of Hydrochloric acid and Acetic acid.

Hydrolysis of 1,2,5,6-Tetrahydropyridine system of Formula VIa in presence of an acid or mixture of acids was carried out at temperature between 40° C. to 110° C. more preferably between 75° C. to 90° C. most preferably between 85° C. to 90° C.

Reductive amination of Formula VIIa can be carried out by using Methylamine in presence of any Lewis acids such as $AlCl_3$, $InCl_3$, Titanium(IV) tetraisopropoxide, $FeCl_3$ etc. more preferably Titanium(IV) tetraisopropoxide.

Reductive amination of Formula VIIa can be carried out by using Methylamine in presence of any Lewis acids in an organic solvent such as alcoholic solvent like Methanol, Ethanol or ethereal solvents like Di-isopropyl ether (DIPE), Methyl tertiary butyl ether (MTB) or Toluene, Xylenes or aqueous mixture(s) thereof more preferably Methanol or water most preferably water.

Reductive amination of Formula VIIa using Methylamine in presence of any Lewis acids in an organic solvent followed by reduction using any reducing agent such as alkali metal borohydride derivatives which includes Sodium borohydride, Sodium cyanoborohydride, Sodium triacetoxyborohydride more preferably Sodium borohydride to produce compound of Formula VIIIa.

Reductive amination of Formula VIIa using Methylamine in presence of any Lewis acids in an organic solvent followed by reduction using any reducing agent or any alkali metal borohydride derivatives to get compound of Formula VIIIa was carried out at temperature between 0° C. to 10° C. more preferably between 0° C. to 5° C.

Resolution of Formula VIIIa in presence of resoluting agent which includes Tartaric acid, Dibenzoyl tartaric acid (DBTA), Ditoluoyl tartaric acid (DTTA), Mandalic acid, Camphor sulphonic acid etc. more preferably Dibenzoyl tartaric acid (DBTA), Ditoluoyl tartaric acid (DTTA) most preferably Ditoluoyl tartaric acid (DTTA) to get compound of Formula IIa Resolution of compound VIIIa in presence of any resoluting agent in an organic solvent includes alcoholic solvent such as Methanol, Ethanol, ethereal solvents, Toluene, Xylenes or aqueous mixture(s) thereof, more preferably methanol to get compound of Formula IIa. Ethereal solvents include Di-isopropyl ether (DIPE), Methyl tertiary butyl ether (MTB) but not limited only to these two solvents. The invention is further illustrated by way of the following examples.

EXAMPLES

Example-1: Preparation of N-(4-methylpyridin-3-yl)-acetamide from 3-Amino-4-methyl pyridine 3-Amino-4-methyl pyridine (200 gm) and Acetic acid (600 mL) were charged in a 2 L 4-neck round bottom flask with an overhead stirrer and stirred for 15 minutes at RT. Acetic anhydride (284 gm/263 mL) or Acetyl chloride (174 gm) was added drop wise within 1-2 h at that temperature. The reaction mass was then stirred at RT for 8-10 h. After the completion of the reaction as monitored by TLC, HPLC; acetic acid was distilled out under vacuum. Methanol (1 L) was then added to the reaction mixture and the pH of the reaction mixture was maintained around 10-12 by liq. Ammonia. Methanol was distilled out completely under vacuum at 50° C. to 55° C. The product was then extracted with MDC (1 L) to get the pure product. Yield: 98% w/w; HPLC Purity: 98%.

Example-2: Preparation of N-(4-methylpyridin-3-yl)-acetamide from 3-Amino-4-methyl pyridine 3-Amino-4-methyl pyridine (200 gm) and Acetic anhydride (284 gm/263 mL) in a 2 L 4-neck round bottom flask with an overhead stirrer were stirred for 15 minutes at RT. The stirring was continued at RT for 1-3 h. After the completion of the reaction as monitored by TLC, Methanol (1 L) was added to the reaction mixture and the pH of the reaction mixture was maintained around 10-12 by liq. Ammonia. Methanol was distilled out completely under vacuum at 50° C. to 55° C. Extraction with MDC (1 L) gave pure product. Yield: 98% w/w; HPLC Purity: 98%.

Example-3: Preparation of N-(4-methylpyridinium-3-yl)-acetamide acetate from 3-amino-4-methyl pyridine 3-Amino-4-methyl pyridine (200 gm), Acetic anhydride (284 gm/263 mL) or Acetyl chloride (174 gm) and MDC (1 L) in a 2 L 4-neck round bottom flask with an overhead stirrer were stirred for 15 minuets at RT. The reaction mass was stirred at RT for 8-10 h. Completion of the reaction was monitored by TLC, HPLC. Extraction with MDC (1 L) gave pure product. Yield: 98% w/w; HPLC Purity: 98%.

Example-4: Preparation of N-(4-methylpyridin-3-yl)-acetamide from 3-Amino-4-methyl pyridine 3-Amino-4-methyl pyridine (200 gm), Acetic anhydride (284 gm/263 mL) or Acetyl chloride (174 gm) and MDC (1 L) in a 2 L 4-neck round bottom flask with an overhead stirrer were stirred for 15 minutes at RT. The reaction mass then stirred at RT for 8-10 h. Completion of the reaction as monitored by TLC. pH of the reaction mixture was maintained around 10-12 by liq. Ammonia. Extraction with MDC (1 L) gave pure product. Yield: 98% w/w; HPLC Purity: 98%.

Example-5: Preparation of 1-Benzyl-4-methyl-1,2,5,6-tetrahydropyridine-3-yl-acetyl amine from N-(4-methylpyridin-3-yl)-acetamide Toluene (1 L) and N-(4-methylpyridin-3-yl)-acetamide (200 gm) were charged in a 2 L 4-neck round bottom flask with an overhead stirrer and stirred for 15 minutes at RT. Benzyl chloride (202 gm) or Benzyl bromide (273 gm) was added to the insoluble reaction mass and stirred for 15 minutes at RT. The temperature of the reaction mass was raised to 80° C. to 85° C. and stirred until the completion of the reaction (monitored by TLC, HPLC). The reaction mass was then cooled to 25° C. to 30° C. and decanted out the toluene layer. Methanol (1 L) was charged to the reaction mixture, stirred to get clear solution and was cooled to 0° C. to 5° C. Sodium borohydride solution (60 gm in 0.1 N Sodium hydroxide) was added drop wise at 0° C. to 5° C. The reaction mixture was then stirred for 10-12 h as required to complete the reaction (monitored by TLC, HPLC). Water (600 mL) was added to the reaction mass and stirred to get clear solution. Distilled out Methanol under vacuum. Solid precipitation observed was filtered by Buckner funnel to get the pure product. (Yield=84-87%; HPLC: 90%).

Example-6: Preparation of 1-Benzyl-4-methyl-1,2,5,6-tetrahydropyridine-3-yl-acetyl amine from N-(4-methylpyridin-3-yl)-acetamide Toluene (1 L), N-acetyl-3-amino-4-methyl pyridine (200 gm) were charged in a 2 L 4-neck round bottom flask with an overhead stirrer and stirred for 15 minutes at RT. Benzyl chloride (202 gm) or Benzyl bromide (273 gm) was added to the insoluble reaction mass and stirred for 15 minutes at that temperature. The temperature of the reaction mass was then raised to 80° C. to 85° C. and stirred the reaction mixture at that temperature for 8-10 h as required to complete the reaction (monitored by TLC, HPLC). The reaction mass was cooled to 25° C. to 30° C. Water (1 L) was charged to the reaction mixture and stirred for 15 minutes. Separated out aqueous layer and cooled it to 0° C. to 5° C. Sodium borohydride solution (60 gm in 0.1 N Sodium hydroxide) was then added into the aqueous layer drop wise at 0° C. to 5° C. The reaction mixture was then stirred for 10-12 h to complete the reaction (monitored by TLC, HPLC). After the completion of the reaction solid precipitation observed was filtered by Buckner funnel to get the pure product. (Yield=84-87%; HPLC: 90%)

Example-7: Preparation of benzyl quarternized salt of N-(4-methylpyridin-3-yl)-acetamide Toluene (1 L), N-(4-methylpyridin-3-yl)-acetamide (200 gm) were charged in a 2 L 4-neck round bottom flask with an overhead stirrer and stirred for 15 minutes at RT. Benzyl chloride (202 gm) or Benzyl bromide (273 gm) was added into the insoluble reaction mass and stirred for 15 minutes at that temperature. The temperature of the reaction mass was then raised to 80° C. to 85° C. and stirred for 8-10 h to complete the reaction (monitored by TLC, HPLC). The reaction mass was then cooled to 25° C. to 30° C. and filtered off the Toluene layer to get pure benzyl quarternized salt of N-(4-methylpyridin-3-yl)-acetamide (Yield=98%; HPLC: 95%)

Example-8: Preparation of 1-Benzyl-4-methyl-1,2,5,6-tetrahydropyridin-3-yl-acetylamine from benzyl quarternized salt of N-(4-methylpyridin-3-yl)-acetamide Methanol (1 L), benzyl quarternized salt of N-(4-methylpyridin-3-yl)-acetamide (200 gm) were charged in a 2 L 4-neck round bottom flask with an overhead stirrer and stirred for 15 minutes at RT. Cooled the reaction mixture to 0° C. to 5° C. and added Sodium borohydride solution (60 gm in 0.1 N Sodium hydroxide) drop wise at that temperature. Stirred for 10-12 h to complete the reaction (monitored by TLC, HPLC). After the completion of the reaction, water (600 mL) was added and stirred to get clear solution. Distilled out methanol under vacuum. Solid precipitation observed was filtered to get the pure product. (Yield=75%; HPLC: 98%).

Example-9: Preparation of 1-Benzyl-4-methyl-1,2,5,6-tetrahydropyridin-3-yl-acetylamine from 3-amino-4-methyl pyridine 3-Amino-4-methyl pyridine (200 gm) and Acetic anhydride (284 gm/263 mL) were charged in a 2 L 4-neck round bottom flask with an overhead stirrer and stirred at 25° C. to 30° C. for 1-3 h. After the completion of the reaction as monitored by TLC, methanol (1 L) was added to the reaction mixture and the pH maintained around 10-12 by liq. Ammonia. Methanol was distilled out completely under vacuum at 50° C. to 55° C. The product was then extracted with MDC (1 L) and distilled out the organic layer to get crude N-(4-methylpyridin-3-yl)-acetamide.

Toluene (1 L) was charged to the reaction mixture and stirred for 15 minutes at RT. Benzyl chloride (202 gm) or Benzyl bromide (273 gm) was added into the insoluble reaction mass and stirred for 15 minutes at that temperature The temperature was then raised to 80° C. to 85° C. and stirred the reaction mixture at that temperature for 8-10 h as required to complete the reaction (monitored by TLC, HPLC). The reaction mass was cooled to 25° C. to 30° C. Water (1 L) was then charged to the reaction mixture and stirred for 15 minutes. Separated out aqueous layer and cooled it to 0° C. to 5° C. Sodium borohydride solution (60 gm in 0.1N Sodium hydroxide) was added into the aqueous layer drop wise at 0° C. to 5° C. The reaction mixture was then stirred for 10-12 h as required to complete the reaction (monitored by TLC, HPLC). After the completion of the reaction solid precipitation observed was filtered by Buckner funnel to get the pure product. (Yield=84-87%; HPLC: 90%).

Example-10: Preparation of N-Benzyl-4-methylpiperidin-3-one from 1-Benzyl-4-methyl-1,4,5,6-tetrahydropyridin-3-yl-acetylamine Acetic acid (50 mL), Conc. HCl 35% (100 mL) were charged in a 2 L 4-neck round bottom flask with an overhead stirrer and stirred for 10 minutes at RT. 1-Benzyl-4-methyl-1,2,5,6-tetrahydropyridin-3-yl-acetylamine (100 gm) was then added into the reaction mass at that temperature. Temperature of the reaction mixture was raised slowly to 85° C. to 90° C. and stirred for 3-4 h at that temperature as required to complete the reaction (monitored by TLC, HPLC). The reaction mixture was cooled to 25° C. to 30° C. and extracted with Toluene (500 mL) to get the pure product. Yield: 95%; HPLC: 95%

Example-11: Preparation of N-Benzyl-4-methylpiperidin-3-one from 1-Benzyl-4-methyl-1,4,5,6-tetrahydropyridin-3-yl-acetylamine Conc. HCl 35% (150 mL) and 1-Benzyl-4-methyl-1,2,5,6-tetrahydropyridin-3-yl-acetylamine (100 gm) were charged in a 2 L 4-neck round bottom flask with an overhead stirrer and stirred for 10 minutes at RT. Temperature of the reaction mixture was raised slowly to 85° C. to 90° C.

and stirred for 3-4 h to complete the reaction (monitored by TLC, HPLC). The reaction mixture was then cooled to 25° C. to 30° C. and extracted with Toluene (500 mL) to get the pure product. Yield: 95%; HPLC: 90%.

Example-12: Preparation of N-Benzyl-4-methylpiperidin-3-one from 1-Benzyl-4-methyl-1,2,5,6-tetrahydropyridin-3-yl-acetylamine Acetic acid (100 mL) and 1-Benzyl-4-methyl-1,2,5,6-tetrahydropyridine-3-yl-acetylamine (100 gm) were charged in a 2 L 4-neck round bottom flask with an overhead stirrer and stirred for 15 minutes at RT. Temperature of the reaction mixture was raised slowly to 85° C. to 90° C. and stirred for 3-4 h to complete the reaction (monitored by TLC, HPLC). The reaction mixture was then cooled to 25° C. to 30° C. and extracted with toluene (500 mL) to get the pure product. Yield: 95%; HPLC: 90%.

Example-13: Preparation of (1-Benzyl-4-methylpiperidin-3-yl)-methylamine from N-Benzyl-4-methylpiperidin-3-one Methanol (500 mL) and N-Benzyl-4-methylpiperid-3-one (100 gm) were charged in a 2 L 4-neck round bottom flask with an overhead stirrer and stirred for 15 minutes at RT. The reaction mass was cooled to 0° C. to 5° C. and Titanium(IV) tetraisopropoxide solution (175 mL) was added drop wise within 30-45 minutes. The reaction mass was stirred at 0° C. to 5° C. for 30 minutes and Methanolic methylamine solution (30%) (100 mL) was added drop wise at 0° C. to 5° C. within 30-45 minutes. The reaction mass was stirred for 2-3 h at 0° C. to 5° C. Sodium borohydride (22 gm) was then added to the reaction mass within 30-45 minutes at 0° C. to 5° C. and stirred for 2-3 h. After the completion of the reaction as monitored by TLC, HPLC; water (500 mL) was added to the reaction mixture and stirred for 30-45 minutes at RT. The product was extracted using MDC (500 mL) to get the pure product. Yield: 90%; HPLC: 90%.

Example-14: Preparation of (1-Benzyl-4-methylpiperidin-3-yl)-methylamine from N-Benzyl-4-methyl-3-piperidone Methanol (500 mL) and N-Benzyl-4-methylpiperid-3-one (100 gm) were charged in a 2 L 4-neck round bottom flask with an overhead stirrer. Stirred for 15 minutes at RT. The reaction mass was cooled to 0° C. to 5° C. and Titanium(IV) tetraisopropoxide solution (175 mL) was added drop wise within 30-45 minutes. The reaction mass was stirred at 0° C. to 5° C. for 30 minutes and Methylamine hydrochloride (66 gm) was added at 0° C. to 5° C. within 30-45 minutes. The reaction mass was stirred for 2-3 h at 0° C. to 5° C. Sodium borohydride (22 gm) was added to the reaction mass within 30-45 minutes at 0° C. to 5° C. and stirred for 2-3 h. After the completion of the reaction as monitored by TLC, HPLC; water (500 mL) was added to the reaction mass and stirred for 30-45 minutes at RT. The product was extracted by using MDC (500 mL) to get the pure product. Yield: 95%; HPLC: 90%.

Example-15: Resolution of (1-Benzyl-4-methylpiperidin-3-yl)-methylamine to get (3R,4R)-(1-Benzyl-4-methylpiperidin-3-yl)-methylamine Methanol (500 mL) and (1-Benzyl-4-methylpiperidin-3-yl)-methylamine (100 gm) were charged in a 2 L 4-neck round bottom flask with an overhead stirrer and stirred for 15 minutes at RT. Ditoluoyl-L-tartaric acid (DTTA) (106 gm) or Dibenzoyl-L-tartaric acid (DBTA) (98 gm) was added to the reaction mixture and stirred for 15 minutes to get clear solution. Water (500 mL) was added to the reaction mass and the temperature was raised to 65° C. to 70° C. and stirred for 1 h. The reaction mass was cooled to 10° C. to 15° C. and maintained for 3 h. The solid precipitated was filtered off to get pure Ditoluoyl-L-tartaric acid (DTTA) or Dibenzoyl-L-tartaric acid (DBTA) salt of (3R,4R)-(1-Benzyl-4-methylpiperidin-3-yl)-methylamine. Yield=80-82%; HPLC: 98%.

Although the present invention recites various specific embodiments, it is not meant to be construed in a limiting sense. Various modifications of the disclosed embodiments and alternate embodiments will become apparent to persons skilled in the art upon reference to the present invention. It is therefore contemplated that such modifications can be made without departing from the true spirit or scope of the present invention as exemplified and claimed herein below.

We claim:

1. A process for preparation of a compound of Formula IIa,

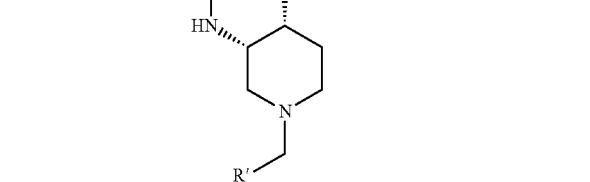

Formula IIa comprising,
(i) N-acylation of 3-Amino-4-methyl pyridine of Formula III with an alkyl acid chloride or acid anhydride to prepare a compound of Formula IVa and optionally isolating it;

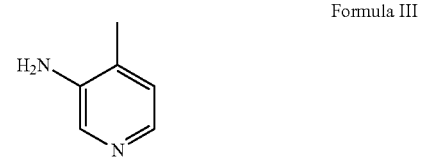

Formula III

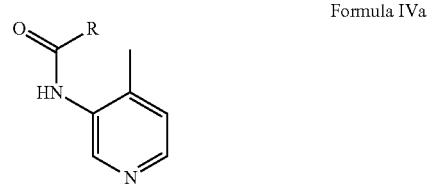

Formula IVa (ii) quarternization of Nitrogen of Pyridine in the compound of Formula IVa, using benzyl halide or substituted benzyl halide in an organic solvent to prepare a compound of Formula Va and optionally isolating it;

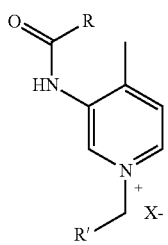

Formula Va (iii) partial reduction of the compound of Formula Va in presence of a reducing agent in a solvent at an ambient temperature to produce a 1,2,5,6- Tetrahydropyridine compound of Formula VIa;

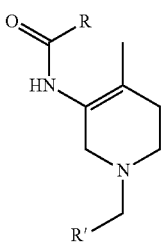

Formula VIa (iv) hydrolysis of the 1,2,5,6-Tetrahydropyridine compound of Formula VIa in presence of an acid or mixture of acids to prepare a compound of Formula VIIa at an ambient temperature or at a temperature ranging from 40° C. to 110° C.;

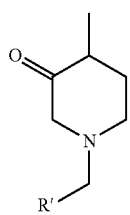

Formula VIIa (v) reductive amination of the compound of Formula VIIa using Methylamine in presence of a Lewis acid in an organic solvent or an aqueous solvent or a mixture thereof, followed by reduction using a reducing agent to prepare a compound of Formula VIIIa at an ambient temperature; and

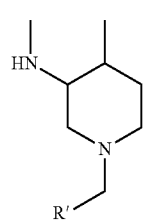

Formula VIIIa (vi) resolution of the compound of formula VIIIa in presence of a resolving agent in an organic solvent or an aqueous solvent or a mixture thereof to prepare the compound of Formula IIa;
wherein R is alkyl; R' is a phenyl or substituted phenyl group; and X represents a halide selected from chloro, bromo, and iodo.

2. The process of claim 1, wherein the alkyl acid anhydride of part (i) is selected from C1-10 acid anhydrides.

3. The process of claim 1, wherein the alkyl acid chloride of part (i) is selected from C1-10 Acid chlorides.

4. The process of claim 1, wherein the benzyl or substituted benzyl halide of part (ii) is selected from the group consisting of Benzyl chloride, Benzyl bromide, substituted Benzyl chloride, and substituted Benzyl bromide.

5. The process of claim 1, wherein the solvent of part (ii) is selected from the group consisting of aromatic solvents, polar aprotic solvents, non-polar solvents, ethers, esters, ketonic solvents, water, and mixture(s) thereof.

6. The process of claim 5, wherein the solvent of part (ii) is selected from the group consisting of Toluene, Xylenes, Cyclohexane, water, and mixture(s) thereof.

7. The process of claim 6, wherein the solvent of part (ii) is selected from the group consisting of Toluene, Xylene, and a mixture thereof.

8. The process of claim 1, wherein the reducing agent of parts (iii) and (v) are selected from the group consisting of Sodium borohydride, Sodium cyanoborohydride, and Sodium triacetoxyborohydride.

9. The process of claim 1, wherein the solvent of part (iii) is selected from the group consisting of water, C1-C5 alcohol, diisopropyl ether, methyl tertiary butyl ether, toluene, xylene, and mixture(s) thereof.

10. The process of claim 1, wherein the acid or mixture of acids of part (iv) is selected from the group consisting of Hydrochloric acid, Sulfuric acid, Phosphoric acid, Trifluoroacetic acid, Trichloroacetic acid, substituted halo acetic acid, Acetic acid, HI, HBr, mineral acids, organic acids, aqueous solutions thereof, and mixture(s) thereof.

11. The process of claim 1, wherein the Lewis acid of part (v) is selected from the group consisting of Aluminium trichloride, Ferric chloride, Zinc chloride, Indium chloride, and Titanium(IV) tetraisopropoxide.

12. The process of claim 1, wherein the resoluting agent of part (vi) is selected from the group consisting of Dibenzoyl tartaric acid, Ditoluoyl tartaric acid, Tartaric acid, Mandelic acid, and Camphor sulphonic acid.

13. The process of claim 1, wherein the organic solvent of part (v) is selected from the group consisting of methanol, ethanol, diisopropyl ether, methyl tertiary butyl ether, toluene, xylene and aqueous mixture(s) thereof.

14. A process for preparation of a compound of Formula Va,

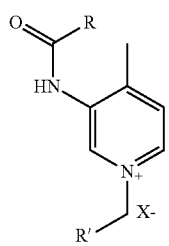

Formula Va comprising, (i) N-acylation of 3-Amino-4-methyl pyridine of Formula III with alkyl acid chloride or acid anhydride to prepare a compound of Formula IVa and optionally isolating it; and

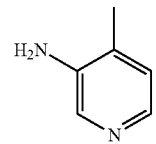

Formula III

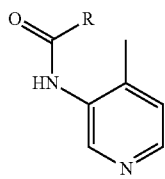

Formula IVa (ii) quarternization of Nitrogen of Pyridine in the compound of Formula IVa, using benzyl halide or substituted benzyl halide in an organic solvent to prepare the compound of Formula Va;

wherein;

the alkyl acid anhydride of part (i) comprises an anhydride of C1-10 acids;

the alkyl acid chloride of part (i) is selected from $C_{1-10}$ acid chloride, or acetyl chloride; the benzyl halide or substituted benzyl halide of part (ii) is selected from the group consisting of Benzyl chloride, Benzyl bromide, substituted Benzyl chloride and substituted Benzyl bromide;

the solvent of part (ii) is selected from the group consisting of aromatic solvents, polar aprotic solvents, non-polar solvents, ethers, esters, ketonic solvents, water and mixture(s) thereof; and R is selected from alkyl; R' is phenyl or substituted phenyl group; and X represents a halide selected from chloro, bromo, and iodo.

15. A process for preparation of a compound of Formula VIa,

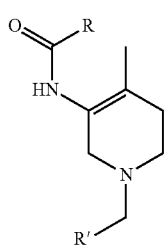

Formula VIa comprising:

(i) N-acylation of 3-Amino-4-methyl pyridine of Formula III with alkyl acid chloride or acid anhydride to prepare a compound of Formula IVa and optionally isolating it;

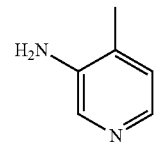

Formula III

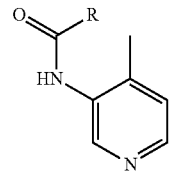

Formula IVa (ii) quarternization of Nitrogen of Pyridine in the compound of Formula IVa, using benzyl halide or substituted benzyl halide in an organic solvent to prepare a compound of Formula Va; and optionally isolating it; and

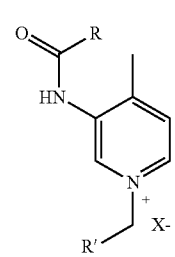

Formula Va (iii) partial reduction of the compound of Formula Va in presence of a reducing agent in a solvent at an ambient temperature to produce the compound of Formula VIa;

wherein;

the alkyl acid anhydride of step (i) comprises an anhydride of a $C_{1-10}$ acid;

the alkyl acid chloride of part (i) is selected from a $C_{1-10}$ Acid chloride, or acetyl chloride; the benzyl halide or substituted benzyl halide of part (ii) is selected from the group consisting of Benzyl chloride, Benzyl bromide, substituted Benzyl chloride and substituted Benzyl bromide;

the solvent of part (ii) is selected from the group consisting of aromatic solvents, polar aprotic solvents, non-polar solvents, ethers, esters, ketonic solvents, water, and mixture(s) thereof;

the reducing agent of part (iii) is selected from the group consisting of Sodium borohydride, Sodium cyanoborohydride, and Sodium triacetoxyborohydride;

the solvent of part (iii) is selected from the group consisting of water, C1-C5 alcohol, DIPE, MTB, Toluene, xylene, and mixture(s) thereof; and R is selected from alkyl; R' is phenyl or substituted phenyl group; and X represents a halide selected from chloro, bromo, and iodo.

16. A process for preparation of a compound of Formula VIIa,

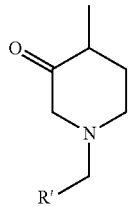
Formula VIIa comprising:

(i) N-acylation of 3-Amino-4-methyl pyridine of Formula III with alkyl acid chloride or acid anhydride to prepare a compound of Formula IVa and optionally isolating it;

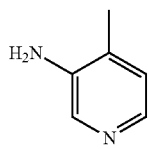
Formula III

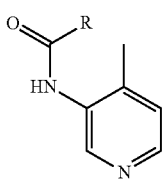
Formula IVa (ii) quarternization of Nitrogen of Pyridine in the compound of Formula IVa, using benzyl halide or substituted benzyl halide in an organic solvent to prepare a compound of Formula Va; and optionally isolating it;

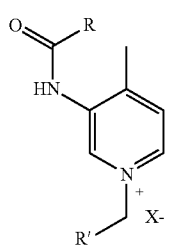
Formula Va (iii) partial reduction of the compound of Formula Va in presence of a reducing agent in a solvent at an ambient temperature to produce 1,2,5,6-Tetrahydropyridine compound of Formula VIa; and

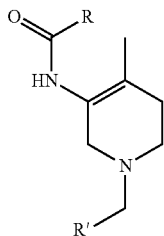
Formula VIa (iv) hydrolysis of the 1,2,5,6-Tetrahydropyridine compound of Formula VIa in presence of an acid or mixture of acids at a temperature ranging from 40° C to 110° C to prepare the compound of Formula VIIa.

wherein;

the the alkyl acid anhydride of part (i) comprises an anhydride of $C_{1-10}$ acids;

the alkyl acid chloride of part (i) is selected from a $C_{1-10}$ Acid chloride, or acetyl chloride; the benzyl halide or substituted benzyl halide of part (ii) is selected from the group consisting of Benzyl chloride, Benzyl bromide, substituted Benzyl chloride and substituted Benzyl bromide;

the solvent of part (ii) is selected from the group consisting of aromatic solvents, polar aprotic solvents, non-polar solvents, ethers, esters, ketonic solvents, water, and mixture(s) thereof;

the reducing agent of part (iii) is selected from the group consisting of Sodium borohydride, Sodium cyanoborohydride, and Sodium triacetoxyborohydride;

the solvent of part (iii) is selected from the group consisting of water, C1-C5 alcohol, DIPE, MTB, Toluene, xylene, and mixture(s) thereof;

the acid or mixture of acids of part (iv) is selected from the group consisting of Hydrochloric acid, Sulfuric acid, Phosphoric acid, Trifluoroacetic acid, Trichloroacetic acid, substituted halo acetic acid, Acetic acid, HI, HBr, aqueous solutions thereof, and mixture(s) thereof; and R is alkyl; R' is phenyl or substituted phenyl group; and X represents a halide selected from chloro, bromo, and iodo.

17. A process for preparation of a compound of Formula VIIIa,

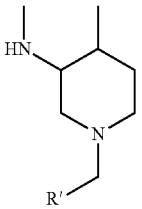
Formula VIIIa comprising, (i) N-acylation of 3-Amino-4-methyl pyridine of Formula III with an alkyl acid chloride or acid anhydride to prepare a compound of Formula IVa and optionally isolating it;

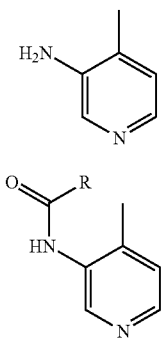

Formula III

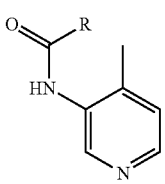

Formula IVa (ii) quarternization of Nitrogen of Pyridine in the compound of Formula IVa, using benzyl halide or substituted benzyl halide in an organic solvent to prepare a compound of Formula Va; and optionally isolating it;

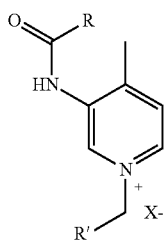

Formula Va (iii) partial reduction of the compound of Formula Va in presence of a reducing agent in a solvent at an ambient temperature to produce a 1,2,5,6-Tetrahydropyridine compound of Formula VIa;

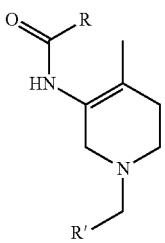

Formula VIa (iv) hydrolysis of the 1,2,5,6-Tetrahydropyridine compound of Formula VIa in presence of an acid or mixture of acids at a temperature ranging from 40° C. to 110° C to prepare a compound of Formula VIIa; and

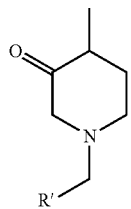

Formula VIIa (v) reductive amination of the compound of Formula VIIa using Methylamine in presence of a Lewis acids in an organic solvent or an aqueous solution or mixture(s) thereof followed by reduction using a reducing agent to prepare the compound of Formula VIIIa at an ambient temperature;

wherein;

the alkyl acid anhydride of part (i) comprises an anhydride of a $C_{1-10}$ acids;

the alkyl acid chloride of part (i) is selected from a $C_{1-10}$ Acid chloride, or acetyl chloride; the benzyl halide or substituted benzyl halide of part (ii) is selected from the group consisting of Benzyl chloride, Benzyl bromide, substituted Benzyl chloride and substituted Benzyl bromide;

the solvent of part (ii) is selected from the group consisting of aromatic solvents, polar aprotic solvents, non-polar solvents, ethers, esters, ketonic solvents, water, and mixture(s) thereof;

the reducing agent of part (iii) is selected from the group consisting of Sodium borohydride, Sodium cyanoborohydride, and Sodium triacetoxyborohydride;

the solvent of part (iii) is selected from the group consisting of water, C1-C5 alcohol, DIPE, MTB, Toluene, xylene, and mixture(s) thereof;

the acid or mixture of acids of part (iv) is selected from the group consisting of Hydrochloric acid, Sulfuric acid, Phosphoric acid, Trifluoroacetic acid, Trichloroacetic acid, substituted halo acetic acid, Acetic acid, HI, HBr, aqueous solutions thereof, and mixture(s) thereof;

the Lewis acid of part (v) is selected from the group consisting of Aluminium trichloride, Ferric chloride, Zinc chloride, Indium chloride, and Titanium(IV) tetraisopropoxide;

the organic solvent of part (v) is selected from the group consisting of methanol, ethanol, DIPE, MTB, toluene, xylene and aqueous mixture(s) thereof; and R is alkyl; R' is phenyl or substituted phenyl group; and X represents a halide selected from chloro, bromo, and iodo.

* * * * *